(12) United States Patent
Heid et al.

(10) Patent No.: US 7,964,141 B2
(45) Date of Patent: Jun. 21, 2011

(54) APPARATUS FOR HANDLING AND CLASSIFYING MICROTOMIZED TISSUE SAMPLES

(75) Inventors: Hans L. Heid, Bammental (DE); Stefan Schock, Oftersheim (DE)

(73) Assignee: Microm International GmbH, Walldorf (DE)

( * ) Notice: Subject to any disclaimer, the term of this patent is extended or adjusted under 35 U.S.C. 154(b) by 379 days.

(21) Appl. No.: 11/919,763

(22) PCT Filed: Mar. 31, 2006

(86) PCT No.: PCT/EP2006/002935
§ 371 (c)(1),
(2), (4) Date: Nov. 1, 2007

(87) PCT Pub. No.: WO2006/119826
PCT Pub. Date: Nov. 16, 2006

(65) Prior Publication Data
US 2009/0087904 A1    Apr. 2, 2009

(30) Foreign Application Priority Data

May 6, 2005    (DE) .......................... 10 2005 021 197

(51) Int. Cl.
*G01N 21/00* (2006.01)
(52) U.S. Cl. .............. 422/65; 422/63; 422/64; 422/500; 422/560; 422/561
(58) Field of Classification Search ............ 422/99–100, 422/63–67, 500, 560–561
See application file for complete search history.

(56) References Cited

U.S. PATENT DOCUMENTS

| 5,122,342 | A | * | 6/1992 | McCulloch et al. ............ 422/65 |
| 5,348,705 | A | * | 9/1994 | Koreyasu et al. ............... 422/67 |
| 5,386,318 | A |   | 1/1995 | Kuhnert |
| 5,690,892 | A |   | 11/1997 | Babler |
| 6,099,230 | A | * | 8/2000 | Hitch ........................ 414/331.02 |
| 2003/0215363 | A1 | | 11/2003 | Metzner |
| 2003/0215936 | A1 | | 11/2003 | Kallioniemi |
| 2004/0253662 | A1 | | 12/2004 | Heid |

FOREIGN PATENT DOCUMENTS

| DE | 102 36 417 | 2/2004 |
| WO | WO 00/62035 | 10/2000 |

* cited by examiner

*Primary Examiner* — Jyoti Nagpaul
(74) *Attorney, Agent, or Firm* — Paul Vincent

(57) ABSTRACT

The invention relates to an apparatus for handling microtomized tissue samples (1) which are arranged on an object carrier (2) and are provided with a machine-readable code (3), with a reader (4) serving to detect the information of the code (3) and a controller (5) serving to convert the information for handling purposes. In order to use such an apparatus to classify unsorted object carriers (2) with respect to one another in a patient-oriented manner for evaluation purposes, it is proposed that a transfer apparatus (6) and at least one drive (7) are provided, which are formed in such a way that they can pick up object carriers (2) from a supply device (8) and move them to a presentation carrier (9) which has receptacles (10) for a plurality of object carriers (2), an apparatus (11) which is ready to hold presentation carriers (9) being arranged and formed in such a way that it keeps a large number of presentation carriers (9) ready in a manner such that they are accessible to the transfer apparatus (6), wherein the controller (5) is formed in such a way that it controls the at least one drive (7) on the basis of the information of the code (3) of the object carrier (2) to the effect that object carriers (2) which originate from a patient can be moved by the transfer apparatus (6) to at least one presentation carrier (9) in an order which is assigned to the patient.

25 Claims, 4 Drawing Sheets

APPARATUS FOR HANDLING AND CLASSIFYING MICROTOMIZED TISSUE SAMPLES

This application is the national stage of PCT/EP2006/002935 filed on Mar. 31, 2006 and also claims Paris Convention priority to DE 10 2005 021 197.6 filed on May 6, 2005.

BACKGROUND OF THE INVENTION

The invention concerns a device for handling microtomized tissue samples which are disposed on an object carrier and are provided with a machine-readable code, with a reader serving to detect the information of the code and a controller serving to convert the information for handling purposes, wherein a transfer device and at least one drive are configured to introduce object carriers to a storage device.

In manual handling procedures, the object carriers can be provided with a code which contains all substantial information needed for evaluation and storage. After cutting, stretching and mounting the sample onto an object carrier, includes drying and deparaffinization of the sample located on the object carrier, further processing takes place, frequently making use of the code. The samples must thereby be dyed, such that the tissue structures are clearly visible under the microscope. After dyeing, the object carrier is covered by a cover glass or another protective layer in order to protect the sample from being damaged. If all tissue samples are equally treated in a standardized process, they can be guided one after the other through the process, thereby maintaining their order and thereby the allocation to a certain patient. When the samples from one patient are processed differently, they must pass through different processing stations or be wetted with different reagents, usually for dyeing. Since the treatment of individual samples with reagents is uneconomical and expensive, the object carriers are sorted into object carrier baskets in accordance with the intended treatment, and such larger amounts thereof can be processed together in an economical fashion. In consequence thereof, any evaluation-oriented allocation with the patient is lost when such a large number of object carriers are processed. It is, however, necessary that the object carriers with the tissue samples of a patient be sorted out from the processed sample tissues, and collected, since all tissue samples of a patient must be available simultaneously for diagnostic evaluation. Towards this end, they are disposed on one or, if required, several presentation carriers. This allocation has been done manually up to now which is laborious and susceptible to errors. Since ever increasing numbers of object carrier codes are only designed as machine-readable codes, manual sorting has become even more difficult.

Devices for carrying out such procedures are not known in the art, rather handling devices for object carriers for different applications.

DE 102 22 333 A1 discloses a handling device for object carriers, which fills plates with object carriers. However, this device does not propose allocation of object carriers and therefore neither detects codes nor requires their information. It merely concerns sequential filling of plates with object carriers provided from a printer.

The device and method according to DE 101 54 843 A1 aim to ensure that the identification of the object carriers comprising microtomized tissue samples coincides with the information of the tissue samples from which they originate, as well as to prevent allocation errors during identification, which involves, at least in part, manual handling. The identification of the microtomized tissue samples can be detected mechanically, but this document does not disclose a device which allocates unsorted object carriers according to some criteria.

US 2003/0215936 A1 discloses a method and a device for automated mass-analysis of microtomized tissue samples. These are thereby disposed on identifiable locations of arrays, which are designed as orthogonal arrangements on carriers, which are, in turn, stacked in several layers. This serves to hold a tissue sample within a spatial matrix composed of a plurality of sample cores defined thereby. The above mentioned device is also suitable for stacking individual object carriers above and next to each other. The problem of allocation of tissue samples to a patient is solved by data processing means, since the evaluation and classification are each performed automatically. Patient-oriented spatial allocation of the microtomized tissue samples is therefore not required, in contrast to manual evaluation. Nor are carrier elements disclosed with which differing object carriers, which are to be processed, can be joined together for simultaneous, patient oriented diagnostic evaluation. Since the preparation device is configured for the acceptance of individual object carriers, the levels also fail to extend in a downward direction to accommodate additional reception area so that the receptive capacity is insufficient to accommodate large numbers of samples.

DE 102 36 417A1 discloses large scale scanning of objects with object carriers being introduced to a scanner and subsequently being archived. Since the electronic images are used for diagnosis, these can be arranged using data processing techniques and presented on a display screen.

U.S. Pat. No. 5,690,892 discloses a handling system for object carriers of the above mentioned kind to remove same from a cassette in which they are stacked, one above the other, and to supply them to a microscope. Subsequent thereto, they can be reintroduced to the same location or to another position in the cassette. Machine readable codes facilitate control.

U.S. Pat. No. 5,386,318 also discloses a handling system for object carriers of the above mentioned kind with which the object carriers are stacked above each other in cassettes which are located in a carousel type magazine. The device is designed to facilitate removal to feed the object carriers to a microscope for observation. However, the removal device can be also used to re-sort the object carriers from one cassette to another. Machine readable codes thereby serve for control of automized operation and handling.

Both handling systems of the above mentioned kind are not suitable for the purpose of diagnostic evaluation, since neither a patient orientated association of the object carriers is carried out, nor are the cassettes suitable for the simultaneous evaluation, in a diagnostic sense, of the samples from a patient and presentation thereof. Visual observation is only possible when the object carriers are removed from the cassettes.

Even the concrete configuration of disposition in cassettes would not solve the problem underlying the present invention. This is the case since, as mentioned above, large numbers of object carriers, which must be processed together, have to be re-orientated and organized with respect to the individual patients. Since economic feasibility is only achieved by large amounts of samples which can be treated in a uniform manner, subsequent ordering to an unacceptably large number of patients must take place. In consequence thereof, the number of patients determines the number of necessary carriers such that a plurality of carriers must be provided for one patient, should the capacity of a carrier be insufficient.

In this regard, the device according to U.S. Pat. No. 5,690,892 is completely unsuitable, since it is not configured for acceptance of a cassette and thereby prohibits association with a large number of separately handleable carriers.

U.S. Pat. No. 5,386,318 also fails to provide suggestions in this direction, although a plurality of cassettes are disposed on a carousel and object carriers can be re-sorted from one cassette to another. In addition to the fact that, as mentioned above, the cassettes are not suitable for the current instant application, an insufficient number can be accommodated on the carousel to facilitate sorting of large quantities. In addition, with such re-sorting, half of the cassettes must be used to provide space for the re-sorted object carriers, such that the other half of the sets located on the carousel can be sorted in a corresponding fashion. This prevents handling of a number of samples needed for economic operation.

The number of carriers necessary for economical operation to receive the object carriers is not satisfied by the above mentioned devices and they are also limited with regard to manual handling.

An individual attempting to associate and identify object carriers from one patient for simultaneous presentation to diagnostic evaluation can however envision use of a large table with the presentation carriers deposited thereon for purposes of such an association. However, the object carriers cannot be sorted within the still larger number of presentation carriers, which requires a larger table. It is not possible to keep track of such a large number of presentation carriers, and the corresponding size of the depositing area required for the presentation carriers is not available in the laboratory and provision thereof would not be economical.

It is therefore the underlying purpose of the present invention to provide for a large number of uniformly handled object carriers whose association with a patient has been lost by collective association for common processing and to do so in an economical fashion which is patient oriented such that simultaneous presentation of the objects coming from a patient is possible for diagnostic evaluation.

SUMMARY OF THE INVENTION

This purpose is achieved in accordance with the invention with a device of the above-mentioned kind which is configured such that the preparation device has shelf-like levels each having presentation carriers disposed next to each other in a y-direction, wherein the presentation carriers each have a plurality of receptacles for the object carriers which are disposed in an x-direction running at right angles hereto, the transfer device being configured for acceptance of the object carriers from an introductory device and for introducing the object carriers into receptacles in that, in a first adjustment motion, the levels, in a second adjustment motion, the presentation carriers, and in a third adjustment motion, the receptacles are approached, wherein the controller is designed in such a fashion that it controls the at least one drive based on information of the code of the object carrier such that object carriers comprising tissue samples which are derived from the same patient, can be moved via the transfer device to at least one presentation carrier in a sequence associated with the patient.

The invention provides an automatic allocation device for moving object carriers comprising samples derived from a plurality of patients, to presentation carriers in a patient-oriented manner to enable diagnostic evaluation of the tissue samples. One presentation carrier is usually used for one patient, but also several may be used, as mentioned above, or if there are only a few tissue samples per patient, the tissue samples of several patients may be provided on one presentation carrier, in this case, of course in an order associated with the individual patients. Since the object carriers are sorted in a processing-oriented fashion, as mentioned above, the tissue samples of a plurality of patients are mixed, such that they are distributed over several processing charges and are processed together with the sample tissues of other patients. For this reason, the inventive allocation device must distribute the object carriers of each incoming processing charge onto many presentation carriers such that each patient has one or more presentation carriers with his/her tissue samples for medical evaluation.

The invention is advantageous in that the amounts of tissue samples, which constantly increase in practice, can be handled without errors, and economically and highly risky, manual allocation can be avoided. In order to provide as many presentation carriers as possible, the presentation carriers have a plurality of levels. Moreover, manual allocation, which is risky, can be avoided. It is also possible to use machine-readable codes only, which would represent a further obstacle for manual allocation. The term code is thereby used for the physical information carrier which may be designed as a label, chip etc. The use of chips is advantageous in that they provide readable data and also receive further data which can be read at any time.

For mass processing, it is particularly advantageous when the preparation device has a rotating carousel type configuration with a plurality of planes in order to increase the number of levels.

In a design, the transfer device comprises a gripper which removes object carriers from the supply device and moves them to a free receptacle of the corresponding presentation carrier via an operating motion. The gripper may also perform a vertical operating motion in order to cooperate with a shelf-like storage device which keeps presentation carriers ready in several planes. Alternatively or additionally, the storage device may provide a water wheel type arrangement of levels so that it can perform the vertical operating motion itself. Automation is advantageously completed in that the storage device is also associated with a supply and discharge device for presentation carriers.

If the reader is not allocated to an upstream station, it is advantageously disposed on the transfer device where the code can be read and the device can perform the corresponding allocation. The codes may thereby contain direct patient allocation or the controller may allocate it by linking the codes of the object carriers with a central file in the central computer. This means that the codes are only provided with an allocation identification and the central file contains all further data relating to the individual patients.

The controller may provide the object carriers to be allocated to a patient to the presentation carrier in consecutive order. If data exists that relates to the tissue samples to be allocated to a patient, the controller may be designed such that it forms a sequence of object carriers comprising the tissues of a patient on the basis of this data. This is advantageous, since the object carriers with the tissue samples possibly arrive in a sequence which does not correspond to the evaluation sequence usually performed by the evaluating person, or which is objectively reasonable or permits economic working, since they are always the same as a standard. Thus, different tissue samples dyes are possibly observed in a preferred sequence. In this case, the controller knows how many object carriers exist from one patient, and how many receptacles must be provided on the presentation carrier for one patient in order to be able to arrange them in sequence. The controller sorts the object carriers in correspondence with the preferred sequence.

The presentation carriers may also comprise at least one code. This code may already contain an identification for direct or indirect patient allocation. In this case, the presentation carriers must either be arranged at predetermined locations in the storage device or the storage device has a reader for the codes of the presentation carriers, such that their placement in the storage device can be detected by the controller in order to allocate the object carriers to the receptacles of the presentation carriers. The storage device may also comprise a write means for entering the information to the codes of the presentation carriers. In this case, the controller may be designed in such a fashion that it writes the patient allocation to the code of an object carrier while it is being moved to the presentation carrier. When the object carriers and the presentation carriers are labelled correspondingly, this double coding can also be used for verification.

A write means may clearly also be provided for entering information to the codes of the object carriers, e.g. in order to also store the classification on the presentation carrier, such that this allocation can be repeated easily in case it is lost during evaluation.

When a central computer is provided, the controller may be designed to store all allocations in a central file of this central computer. A display with clarifying messages may be provided to check the function of the device. An input device may also be provided for effecting later changes.

The supply device may be designed for subsequent supply of individual object carriers to the transfer device. This is advantageous when the inventive device is e.g. directly coupled to a covering device which covers the object carriers with cover glasses. In this case, the supply device may e.g. be a conveyor belt between the covering device and the inventive device.

The supply device may alternatively be arranged to supply magazines comprising object carriers and the transfer device may be arranged to remove object carriers from the magazines. In this case, it is of course also useful to provide a discharge means for empty magazines. The magazines can also be transported using conveyor belts. The transfer device must then clearly be arranged to be able to remove the object carriers from the magazines. This is possible using e.g. a gripper. It is also possible to provide a slider which pushes the object carriers out of the magazine as in a slide projector magazine.

The transfer device can be designed in numerous ways. The exact design depends on whether individual object carriers are supplied or whether magazines with object carriers are supplied, as mentioned above. Since there are numerous possibilities of designing a transfer device of this type, two embodiments are mentioned below by way of example:

The transfer device may be a ramp which receives the object carriers from the supply device, wherein an operating motion allocates the ramp exit to a free receptacle of a presentation carrier, and a displacement device is provided which pushes the object carrier from the ramp. A transfer device of this type must clearly contain different drives for the operating motions in order to move the ramp exit to the corresponding presentation carrier and to a free receptacle thereon. It is of course also possible to move the storage device including presentation carriers and the respective free receptacle below the ramp exit. Additionally, a drive for the displacement device must be provided, such that the object carrier can be moved into the free receptacle.

A detector may also be provided on the transfer device for identifying unusable object carriers. Air bubbles may e.g. be produced by covering, which render a tissue section unsuitable for evaluation. Such object carriers should be removed and replaced or post-processed. Towards this end, the controller causes the transfer device to move object carriers, which are unusable or cannot be allocated, into a reject container. This method sorts out object carriers with tissue samples without patient allocation, since they contain no presentation carrier for the patient or no file for providing a presentation carrier for a patient.

BRIEF DESCRIPTION OF THE DRAWING

The invention is explained below with reference to the embodiments shown in the drawing.

DESCRIPTION OF THE PREFERRED EMBODIMENT

Figure 1:
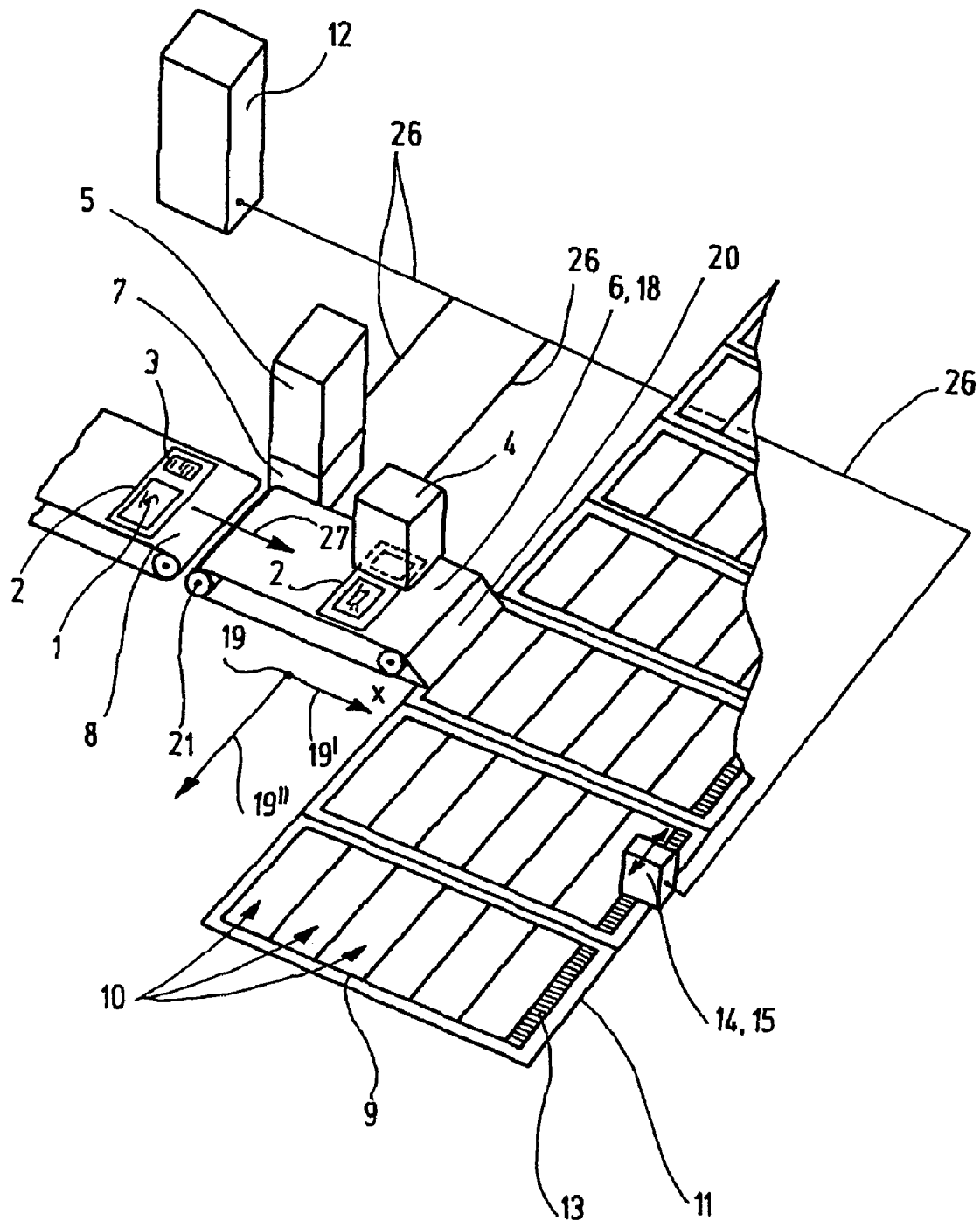
FIG. 1 shows a first embodiment of a transfer device and a detailed configuration of object and presentation carriers.
Figure 2A:
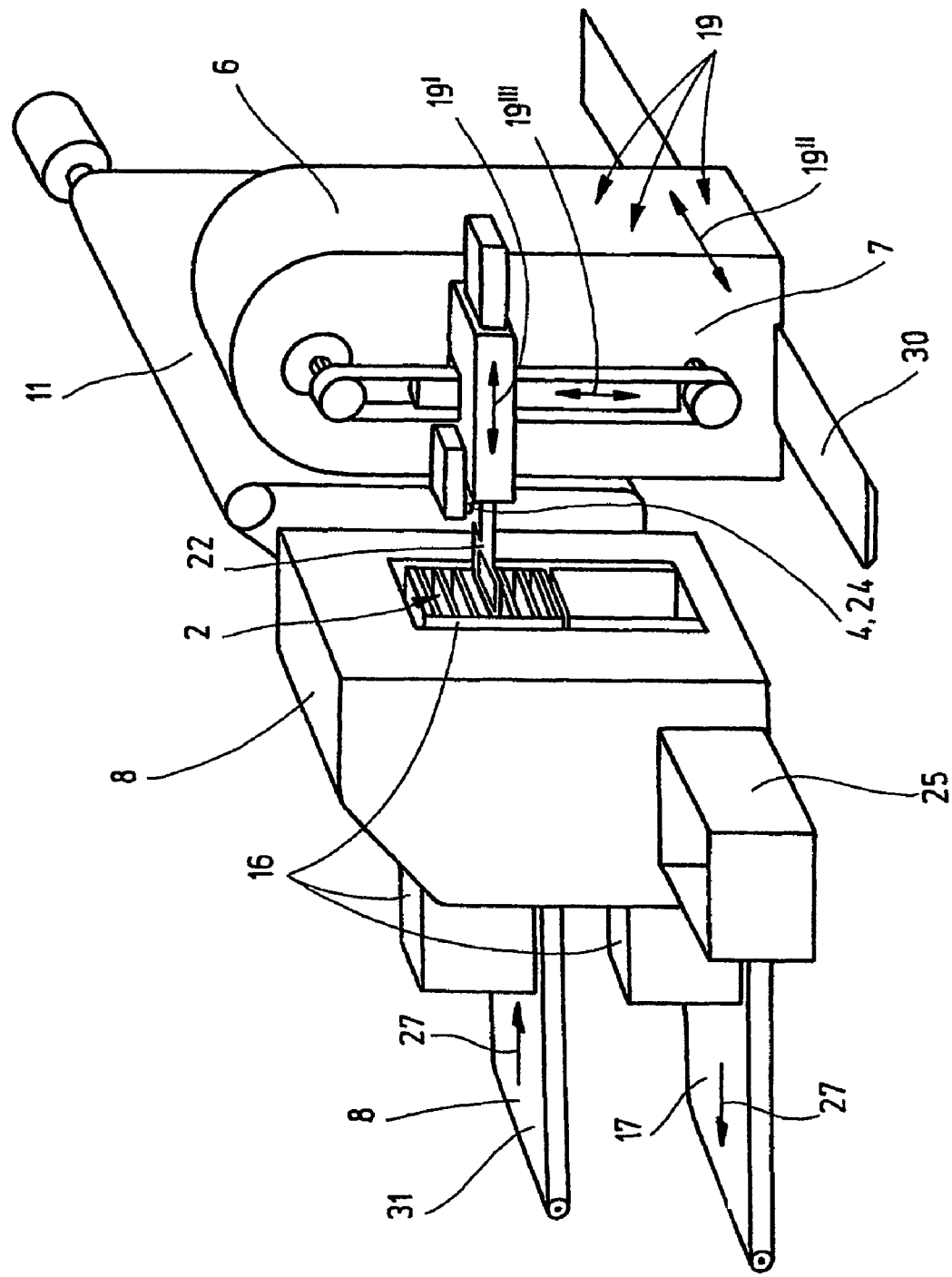
FIGS. 2a and 2b show a second embodiment of the invention.
Figure 2B:
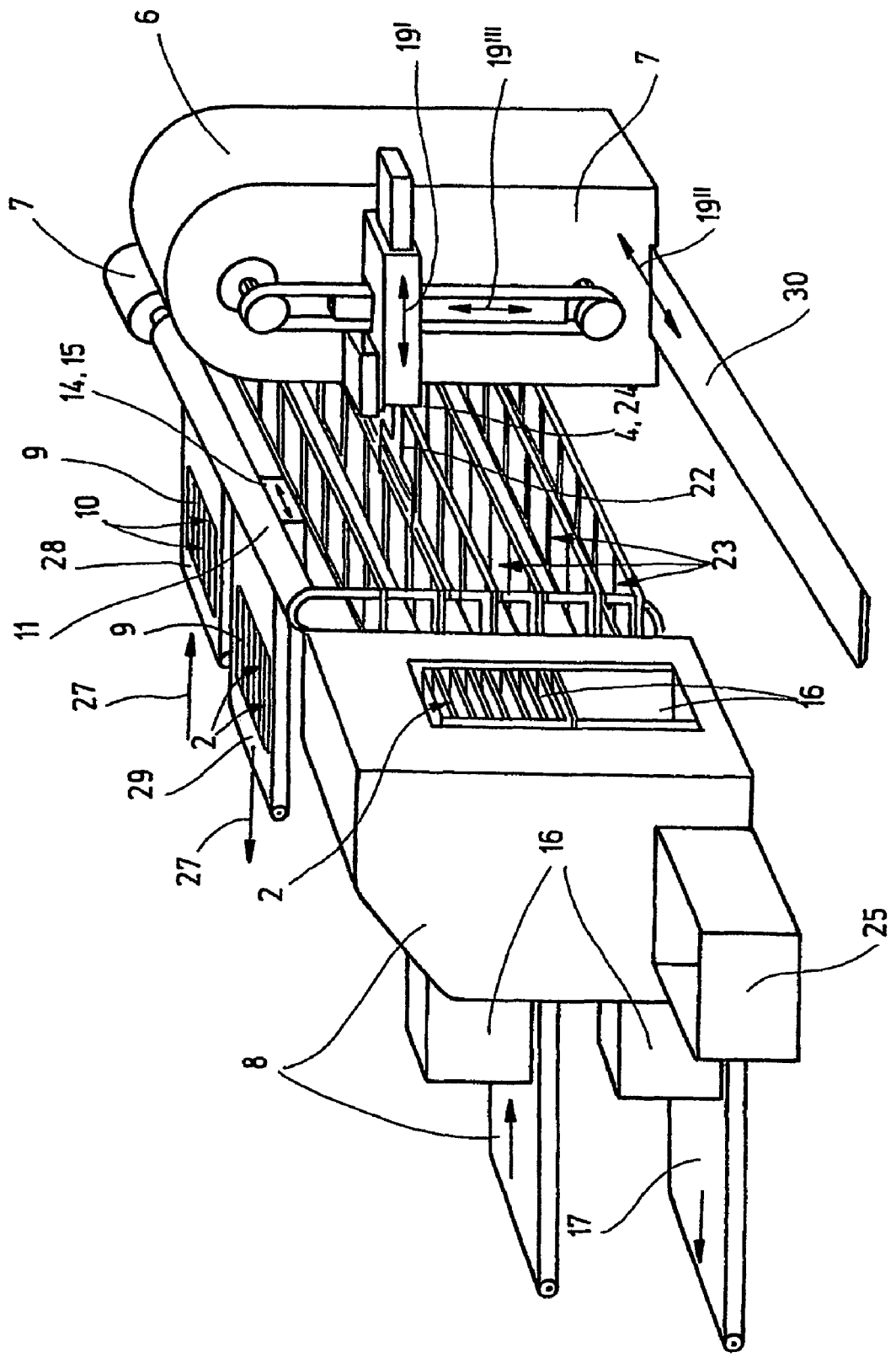

FIG. 1 shows a first embodiment of the inventive device 6 as well as a detailed embodiment of object carries 2 and presentation carries 9. This embodiment of a transfer device 6 can, for example, cooperate with a preparation device 11 as shown in FIGS. 2a and 2b, wherein the ramp 18 must then be introduced between the levels 23.

Tissue samples 1 are supplied to the device via a supply device 8, the tissue samples being located on object carriers 2 and having a code 3. The supply device 8 transfers the object carriers 2 to a transfer device 6 which is provided with a reader 4. The reader 4 detects the code 3 and transfers the information either directly to a controller 5 or to a central computer 12 via a signal line 26. Based on the code information, the controller 5 immediately becomes operative or the central computer 12 contains corresponding data on the basis of which the controller 5 becomes operative. The controller 5 thereby causes the drives 7 to perform operating motions 19, one operating motion 19' in the x direction and one operating motion 19" in the y direction. The latter serves to allocate the transfer device 6 to a presentation carrier 9 which is located on a storage device 11. A reader 14 which may also be designed as a write means 15 is disposed on the storage derive 11 for this allocation. It serves to either detect or label the code 13 of the presentation carrier 9. A signal line 26 also extends from the reader 14 and optionally also from the write means 15 to the controller 5 or the central computer 12. An object carrier 2 can be allocated with a presentation carrier 9 in this fashion, which is either allocated to a patient via a code 3 or is allocated to a patient using the write means 15 when object carriers 2 are to be positioned thereon, which are allocated to a patient.

In order to be able to dispose the object carriers 2 on the presentation carriers 9, the transfer device 6 is designed as a ramp 18 with a ramp exit 20 which can be displaced by an operating motion 19' in the x-direction to supply an object carrier 2 to one of several receptacles 10 of a presentation carrier 9. If the ramp exit 20 has been allocated to a receptacle 10 of a presentation carrier 9, a displacement device 21, designed as a belt in the present case, is activated and transports the object carrier 2 into the corresponding receptacle 10. The transport direction of the transfer device 6 and of the supply device 8 is indicated by arrow 27. When the object carrier 2 is supplied into the corresponding receptacle 10 of the corresponding presentation carrier 9, the transfer device 6 returns into its initial position in order to receive the next object carrier 2 from the supply device 8.

The transfer device 6 can clearly also be stationarily installed. In this case, a drive 7 ensures that the storage device 11 is displaced such that the ramp exit 20 is allocated to the corresponding receptacle 10 of the corresponding presentation carrier 9.

FIGS. 2a and 2b show a further embodiment of the invention. The design of the object carrier 2 and of the presentation carrier 9 thereby correspond to the illustrations and descriptions of FIG. 1, but are only symbolically shown. The controller 5 and the central computer 12 also correspond to the illustrations and implementations of FIG. 1, but are not shown either. The signal lines 26 are also not shown.

FIG. 2a shows the cooperation between a transfer device 6 with gripper 22 and a supply device 8 which is designed to supply magazines 16 in which the object carriers 2 are disposed. These are a plurality of object carriers 2 which are disposed in the magazines 16 such that they can be inserted and removed. The magazines 16 may e.g. be those which collect object carriers 2 for common treatment of the tissue samples 1, e.g. in a dye bath. The magazines 16 are supplied via a conveyor belt 31 and are provided by the supply device 8 such that the gripper 22 can grasp the object carriers 2. The gripper 22 is thereby only symbolically shown, an e.g. tong-like gripper mechanism must be imagined. The gripper 22 comprises a reader 4 which may also be designed as a write means and may additionally be designed as a detector 24.

The object carriers 2 are allocated using the controller 5 and optionally using the central computer 12 as described in connection with FIG. 1. The detector 24 is additionally provided, which serves to move the object carriers 2 which are unusable, or object carriers 2 which cannot be allocated to a patient, into a reject container 25.

When a magazine 16 has been emptied, it is transported away using a discharge means 17. The arrows 27 show the transport direction of the discharge means and of the conveyor belt 31. When the gripper 22 has grasped an object carrier 2 and the latter was read by the reader 4 and was not sorted out, the transfer device 6 moves the object carrier 2 to a receptacle 10 of a presentation carrier 9. This is effected by a guide 30 on which the transfer device 6 is disposed in a displaceable fashion, and by different operating motions 19. These are the operation motion 19' which serves to remove the object carrier 2 from the magazine 16 and is followed by an operating motion 19" which moves the transfer device 6 to the storage device 11 along the guide 30. The storage device 11 is thereby only symbolically shown. These operating motions are performed by drives 7 which may be housed in the housing of the transfer device 6.

The cooperation between the transfer device 6 and the storage device 11 for sorting the object carriers 2 is shown in FIG. 2b. This figure also shows the storage device 11 in detail, which also comprises a drive 7 that circulates the levels 23 in a water-wheel fashion.

A supply device 28 initially introduces the presentation carriers 9 in the transport direction 27 to the storage device 11. Following filling with object carriers 2, the removal device 29 then removes the filled presentation devices 9.

The presentation carriers 9 can already be provided with patient allocations via codes 13 (not shown herein), which are detected by a reader 14 so that the object carriers 2 can be allocated to corresponding receptacles 10 of the corresponding presentation carriers 9 using the controller 5 and optionally using the central computer 12. Alternatively, a write means 15 may be activated while the object carriers 2 are supplied to the receptacles 10 of the presentation carriers 9, which correspondingly enters this allocation into the code 13 of the presentation carriers 9. The reader 14 and write means 15 must be disposed to be displaceable, as in FIG. 1, in order to detect each code 13 of each presentation carrier 9.

After determination of the allocation, the gripper 22 moves to the corresponding plane 23 on which the presentation carrier 9 is located, into the receptacles 10 of which the object carriers 2 of a certain patient are to be placed. This motion towards the corresponding plane 23 can be performed by the operating motion 19''' or this allocation may also be produced by a water wheel-like adjustment of the planes 23. The operating motion 19' is then activated so that the gripper 2 can move the object carrier 2 into the corresponding free receptacle 10 of the presentation carrier 9.

The transfer device 6 is subsequently returned to the supply device 8 using the guide 30 and the operating motion 19" to receive the next object carrier 2.

Figure 3:
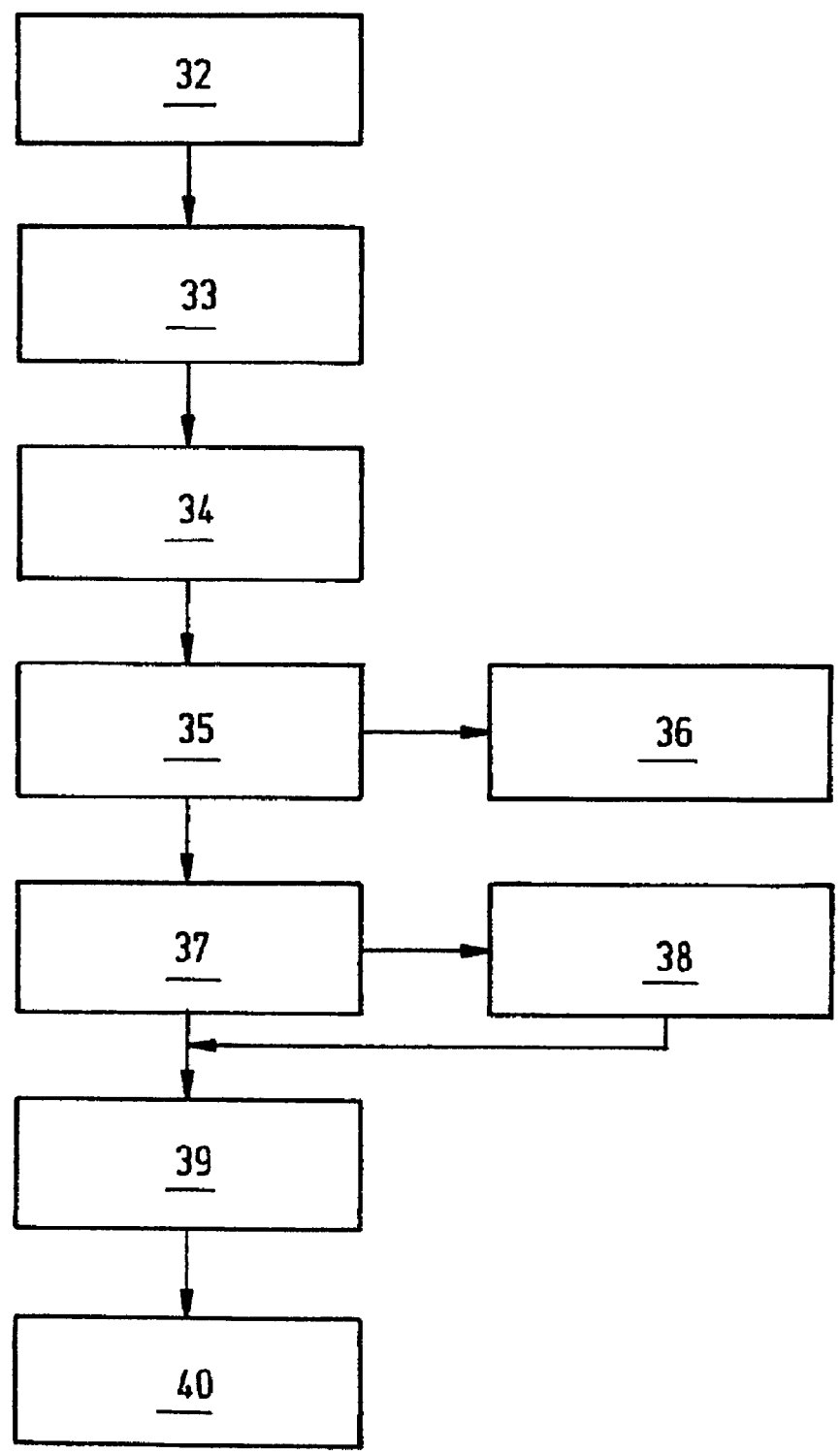
FIG. 3 shows a diagram of potential work steps of an inventive device.

FIG. 3 shows a diagram of feasible work steps of an inventive device. The following steps are provided:

32 providing presentation carriers 9 in the storage device 11
33 supplying an object carrier 2
34 receiving the object carrier 2 via the transfer device 6
35 reading and detecting the object carrier 2
36 sorting out object carriers 2, which are unusable or cannot be allocated, into the reject container 25
37 identified presentation carrier present?
38 no: identification of a presentation carrier
39 yes: transfer and classifying to receptacle 10
40 return in order to classify the next object carrier The embodiments show the different designs of the device. It may be provided only with a controller 5 or may additionally include a central computer 12. The supply device 8 of the design of FIG. 1 may also be provided in the embodiment of FIGS. 2a and 2b and vice versa. The transfer device 6 can also be transferred from FIG. 1 to FIGS. 2a and 2b and vice versa. Only a slider must be provided which supplies the object carriers 2 from the magazine 16 onto the ramp 18. When the transfer device 6, designed as a ramp 18, cooperates with a storage device 11 as is shown in FIGS. 2a and 2b, the ramp 18 would clearly have to be insertable between the planes 23. A gripper 22, a supply device 28 and a discharge device 29 for presentation carriers 9 may clearly also be provided as the transfer device 7 in FIG. 1.

It is obvious that many features can be mutually exchanged. Completely different solutions are clearly also possible, e.g. to transport object carriers 2 via a slide whose output is then allocated to the corresponding receptacle 10 of a presentation carrier 9. Further variants are feasible.

LIST OF REFERENCE NUMERALS

1 tissue samples
2 object carrier
3 code (object carrier)
4 reader
5 controller
6 transfer device
7 drives
8 supply device for object carriers or magazines
9 presentation carriers
10 receptacles for several object carriers
11 storage device
12 central computer
13 code (presentation carrier)
14 reader
15 write means
16 magazine 17 discharge means for magazines
18 ramp
19 operating motions
19' arrow: operating motion in x direction
19" arrow: operating motion in y direction
19'" arrow: operating motion in z direction (height)
20 ramp exit
21 displacement device
22 gripper
23 levels
24 detector
25 reject container
26 signal lines
27 transport direction
28 supply device for presentation carriers
29 discharge device for presentation carriers
30 guide of the transfer device
31 conveyor belt

We claim:

1. A device for handling microtomized tissue samples disposed on object carriers having a machine-readable code, the device comprising:
    a reader to detect information of the code;
    a controller to process the code information, said controller structured to allocate unsorted object carriers with respect to each other for evaluation purposes in a patient-oriented manner;
    at least one drive for transporting the object carriers;
    a transfer device to receive the object carriers;
    a supply device for feeding the object carriers to said transfer device; and
    a storage device structured for receiving object carriers from said transfer device,
    said storage device having a plurality of shelf-like storage device levels stacked, one upon another, in a vertical z-direction, said storage device also having a plurality of presentation carriers disposed next to each other on said storage device levels in a horizontal y-direction, wherein each presentation carrier has a plurality of receptacles for the object carriers, said receptacles being disposed in a horizontal x-direction extending at right angles to said y-direction, said transfer device being structured for carrying out a vertical operating motion in which an object carrier is introduced to one said level, a first horizontal operating motion in which that object carrier is introduced to one said presentation carrier, and a second horizontal operating motion in which that object carrier is introduced into one said receptacle, wherein said controller is structured to control said at least one drive based on information of the object carrier code such that object carriers comprising tissue samples from a same patient are moved via said transfer device to at least one said presentation carrier in a sequence associated with the patient.

2. The device of claim 1, wherein said storage device has a Ferris wheel-like arrangement of levels to increase a number of said levels.

3. The device of claim 1, wherein said transfer device comprises a gripper which removes object carriers from said supply device or from a magazine disposed thereon, and moves them to a free receptacle of said presentation carrier via an operating motion.

4. The device of claim 3, wherein said gripper also performs a vertical operating motion to cooperate with said shelf-like storage device.

5. The device of claim 4, wherein said storage device has a water wheel-like arrangement of said levels to execute said vertical operating motion.

6. The device of claim 1, wherein said storage device has an associated supply and discharge device for said presentation carriers.

7. The device of claim 1, wherein said reader is disposed on said transfer device.

8. The device of claim 1, wherein the codes directly contain a patient allocation.

9. The device of claim 1, wherein said controller performs an allocation by linking the code with a central file in a central computer.

10. The device of claim 1, wherein said controller provides the object carriers allocated to a patient to said presentation carrier in a continuous sequence.

11. The device of claim 1, wherein said controller forms a sequence of object carriers with tissues of a patient based on predetermined data.

12. The device of claim 1, wherein said presentation carriers also comprise at least one code.

13. The device of claim 12, wherein codes already contain an identification for direct or indirect patient allocation.

14. The device of claim 12, wherein said storage device comprises a reader for codes of said presentation carriers.

15. The device of claim 12, wherein said storage device comprises a write means for entering information into the codes.

16. The device of claim 15, wherein said controller is structured to write the code, including patient allocation, to an object carrier while moving it to said presentation carrier.

17. The device of claim 1, further comprising a write means for entering information to codes of the object carriers.

18. The device of claim 1, wherein said controller is structured to store all allocations in a central file of a central computer.

19. The device of claim 1, further comprising a display for clarifying messages.

20. The device of claim 1, wherein said supply device is structured for subsequent supply of individual object carriers to said transfer device.

21. The device of claim 1, wherein said supply device is structured to supply magazines with object carriers and said transfer device is structured to remove objects carriers from said magazines.

22. The device of claim 21, further comprising a discharge device for empty magazines.

23. The device of claim 1, wherein said transfer device comprises a ramp to which said supply device transfers the object carriers, an operating motion allocating a ramp exit to a free said receptacle of said presentation carrier as well as a displacement device to push the object carriers from said ramp.

24. The device of claim 1, further comprising a detector disposed on said transfer device for identifying unusable object carriers.

25. The device of claim 1, wherein said controller causes said transfer device to transfer object carriers, which are unusable or which cannot be allocated, to a reject container.

* * * * *